United States Patent [19]

Stockinger et al.

[11] 4,218,377
[45] Aug. 19, 1980

[54] METAL SALT/AMINE COMPLEXES

[75] Inventors: Friedrich Stockinger, Hölstein; Sameer H. Eldin, Birsfelden; Friedrich Lohse, Oberwil, all of Switzerland

[73] Assignee: Ciba-Geigy Corporation, Ardsley, N.Y.

[21] Appl. No.: 956,521

[22] Filed: Oct. 31, 1978

[30] Foreign Application Priority Data

Nov. 4, 1977 [CH] Switzerland .................... 13447/77

[51] Int. Cl.$^2$ ............................................ C07D 403/02
[52] U.S. Cl. ............................ 260/326.22; 260/429 R; 260/429 CY; 260/429.9; 260/438.1; 260/439 R; 260/439 CY; 528/102; 528/108; 528/109; 528/111; 528/112; 528/114; 528/117; 528/120; 528/121; 528/406; 528/407; 528/418; 528/421
[58] Field of Search ............ 260/326.22, 438.1, 429.9, 260/429 CY, 429 R, 439 CY, 439 R

[56] References Cited

U.S. PATENT DOCUMENTS

| | | | |
|---|---|---|---|
| 2,686,798 | 8/1954 | Gmitter | 260/429.9 |
| 2,924,551 | 2/1960 | Harwood et al. | 260/438.1 |
| 3,310,602 | 3/1967 | Lemon et al. | 260/429.9 |
| 3,351,647 | 11/1967 | Butler et al. | 260/438.1 |
| 3,355,466 | 11/1967 | Elkin | 260/429.9 |
| 3,914,266 | 10/1975 | Hay | 260/438.1 |

*Primary Examiner*—Mary C. Lee

*Attorney, Agent, or Firm*—Joseph F. DiPrima; Harry Falber

[57] ABSTRACT

Novel carboxylic acid metal salt/amine complexes of the formula

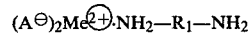

in which A is the anion of cyanoacetic acid, pyrrolidonecarboxylic acid, maleimidylcarboxylic acid, succinylimidylcarboxylic acid, benzenesulphonic acid or toluenesulphonic acid or of a methanephosphonic acid monoester or benzenephosphonic acid monoester, $Me^{2+}$ is a divalent metal cation and $R_1$ is a long-chain polyoxyalkylene radical, are obtained by reacting 1 mol of a carboxylic acid metal salt of the formula

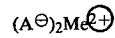

with 1 mol of a diamine of the formula $$H_2N-R_1-NH_2$$

in a polar organic solvent and in the temperature range of 25° to 200° C. to give the complex compounds of the formula.

The novel complex compounds are valuable curing agents for epoxide resins and in mixtures with epoxide resins have an advantageous storage stability.

6 Claims, No Drawings

METAL SALT/AMINE COMPLEXES

The present invention relates to carboxylic acid metal salt/amine complexes, a process for their preparation and the use of the novel complex compounds as curing agents for epoxide resins.

Metal complexes of aliphatic carboxylic acids with diethylenetriamine and their use as curing agents for epoxide resins are known from U.S. Pat. No. 2,819,233. However, these known metal complexes have the disadvantage that they have a relatively low stability on storage when mixed with epoxide resins. Moreover, relatively long curing times are required for complete crosslinking of the epoxide resin mixtures containing these complexes.

In Japanese Patent Publication No. 24,397/75 it is also proposed to cure epoxide resins with a curing agent combination consisting of carboxylic acid salts and amines. This curing agent combination does indeed have good storage stability when mixed with epoxide resins, but the curable mixtures give moulded materials which have low mechanical strength and poor dielectric properties.

It has now been found that metal salts of specific carboxylic acids can be reacted with long-chain diamines containing a polyoxyalkylene radical to give complex compounds which do not have the disadvantages described above or have these disadvantages to a lesser extent. The storage stability of the novel complex compounds when mixed with epoxide resins is far better, and the cured moulded materials have better mechanical and especially dielectric properties.

The present invention thus relates to novel metal salt/amine complexes of the formula I $$(A^{\ominus})_2 Me^{\oplus\oplus} \cdot NH_2-R_1-NH_2 \qquad (I)$$

in which A is an anion which contains a polar acyl radical and has the formula

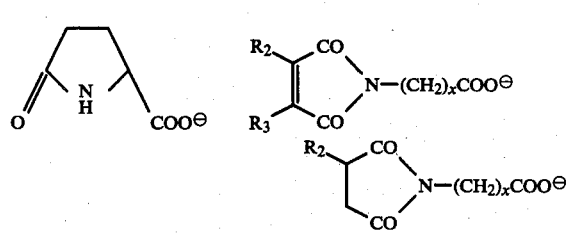

in which x=a number from 1 to 5 in each case and $R_2$=H or methyl,

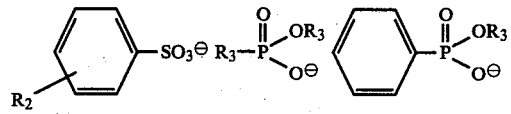

in which $R_2$=—H or methyl and $R_3$=alkyl having 1 to 4 C atoms in each case, or N≡C—CH$_2$—COO$^\ominus$, Me$^{\oplus\oplus}$ is a divalent metal cation and $R_1$ is a polyoxyalkylene radical of the formula

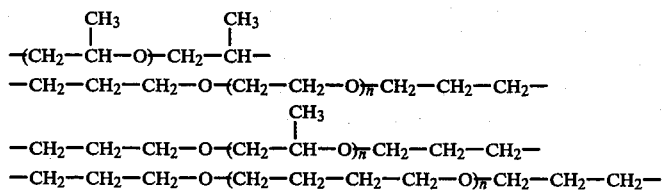

in which n=a number from 2 to 35 in each case, or

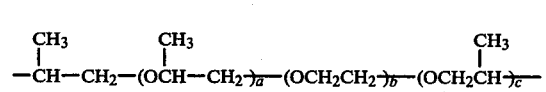

in which b=a number from 10 to 50 and the sum of a and c is a number from 2 to 4.

A in formula I is preferably an anion which contains a polar acyl radical and has the formula

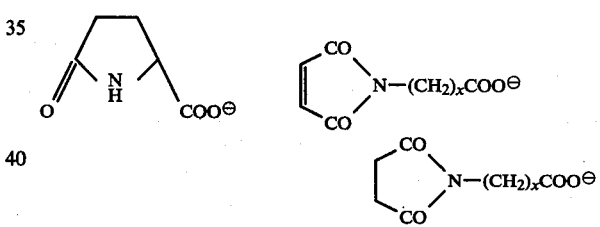

in which x=a number from 1 to 5 in each case,

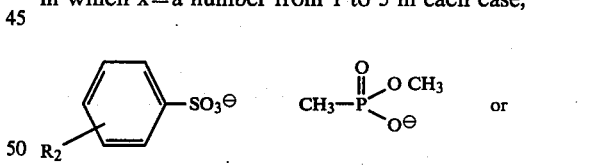

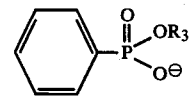

in which $R_2$=—H or methyl and $R_3$=alkyl having 1 to 4 C atoms in each case.

A in formula I is in particular the anion of pyrrolidonecarboxylic acid, benzenesulphonic acid or toluenesulphonic acid or of a methanephosphonic acid monoester and particularly preferentially is the anion of pyrrolidonecarboxylic acid or benzenesulphonic acid.

Compounds of the formula I in which Me$^{\oplus\oplus}$ is a divalent metal cation of Zn, Co, Cu, Ni or Cd, especially Zn, are also preferred compounds. Furthermore, in formula I, the radical $R_1$ is preferably a polyoxyalkylene radical of the formula

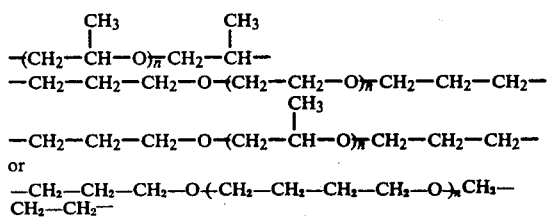

and especially the polyoxyalkylene radical of the formula

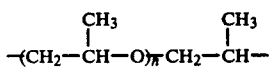

in which formulae n is a number from 2 to 35.

The novel metal salt/amine complexes of the formula I are obtained by reacting 1 mol of a carboxylic acid metal salt of the formula II $$(A^\ominus)_2 Me^{2\oplus} \qquad (II)$$

in which A and $Me^{2\oplus}$ are as defined in formula I, with 1 mol of a diamine of the formula III $$H_2N-R_1-NH_2 \qquad (III)$$

in which $R_1$ is as defined in formula I, in a polar organic solvent and in the temperature range of 25° to 200° C., preferably 50° to 150° C.

Carboxylic acid metal salts of the formula II preferably used in this process are those in which A is an anion which contains a polar acyl radical and has the formula

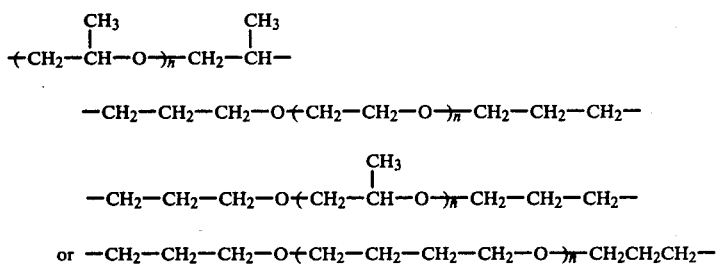

in which x=a number from 1 to 5 in each case,

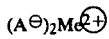

or

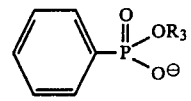

in which $R_2 = -H$ or methyl and $R_3$=alkyl having 1–4 C atoms in each case, and especially those in which A is the anion of pyrrolidonecarboxylic acid, benzenesulphonic acid or toluenesulphonic acid or of a methanephosphonic acid monoester.

Carboxylic acid metal salts of the formula II in which $Me^{2\oplus}$ is a divalent metal cation of Zn, Co, Cu, Ni or Cd, especially Zn or Ni, are likewise compounds which are preferably used.

Diamines of the formula III which are preferably employed are those in which $R_1$ is a polyoxyalkylene radical of the formula

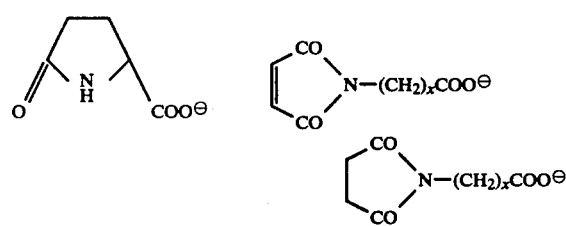

in which n is a number from 2 to 35 in each case, and especially those in which $R_1$ is a radical of the formula

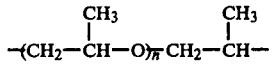

in which n is a number from 2 to 35.

The carboxylic acid metal salts of the formula II are known compounds which are obtained by reacting 2 mols of carboxylic acid with 1 mol of the corresponding metal oxide, with the elimination of water, or by reacting the carboxylic acid Na salts with the corresponding metal salts of inorganic acids. A process of this type is described, for example, in "Helvetica Chimica Acta" 8, 1925, page 369–383.

The diamines of the formula III are also known compounds. The diamines of the formula III in which $R_1$ is a radical of the formula

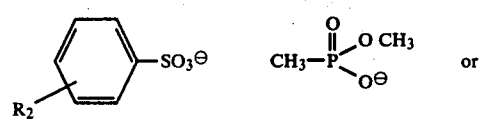

or of the formula

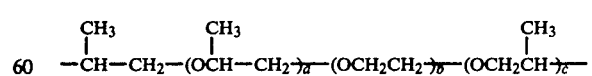

are available commercially under the tradename "Jeffamine" from Jefferson Co. The diamines of the formula III in which $R_1$ is one of the other polyoxyalkylene radicals are obtained by adding on 2 mols of acrylonitrile to 1 mol of the corresponding polyoxyalkylene glycol and subsequently reducing the nitrile groups to amino groups.

Polar organic solvents suitable for the process for the preparation of the compounds of the formula I are alcohols, ketones, ethers and esters and also mixtures thereof. Examples are: glycols, especially diethylene glycol, acetone, methyl ethyl ketone, dioxan, tetrahydrofuran, dipropyl ether, dibutyl ether, ethylene glycol monoethyl ether, ethylene glycol mono-n-butyl ether, ethylene glycol dimethyl ether and the like. The more strongly polar solvents, such as dimethylformamide, dimethylacetamide and dimethylsulphoxide, are generally preferably employed.

The amount of solvent to be employed in the process is not critical as long as the amount is sufficient to dissolve the starting materials therein. In general, the reaction is carried out using 20 to 60 percent by weight solutions, based on the amount of the starting materials.

The complex compounds according to the invention are valuable curing agents for epoxide resins, and the complex compounds can be employed either in catalytic amounts or in equivalent amounts, depending on which processing characteristics or end characteristics are preferred for the curable or, respectively, cured epoxide resin mixtures.

The catalytic amount used is preferably 3–15 parts of the complex compound per 100 parts of epoxide resin. If equivalent amounts of the complex compounds are used as curing agents, 0.8 to 1.3 equivalents of amine hydrogen atom are used per 1 epoxide equivalent.

The present invention thus also relates to the use of the complex compounds according to the invention as curing agents for epoxide resins.

All the known categories of epoxide resins are suitable as epoxide resins which can be cured using the complex compounds according to the invention. In particular, the epoxide resins are epoxide compounds which contain, on average, more than one glycidyl group, $\beta$-methylglycidyl group or 2,3-epoxycyclopentyl group bonded to a heteroatom (for example sulphur and preferably oxygen or nitrogen); preferred compounds are bis-(2,3-epoxycyclopentyl) ether; di- and poly-glycidyl ethers of polyhydric aliphatic alcohols, such as 1,4-butanediol, or polyalkylene glycols, such as polypropylene glycols; di- or poly-glycidyl ethers of cycloaliphatic polyols, such as 2,2-bis-(4-hydroxycyclohexyl)-propane; di- and poly-glycidyl ethers of polyhydric phenols, such as resorcinol, bis-(p-hydroxyphenyl)-methane, 2,2-bis-(p-hydroxyphenyl)-propane (=diomethane), 2,2-bis-(4'-hydroxy-3',5'-dibromophenyl)-propane or 1,1,2,2-tetrakis-(p-hydroxyphenyl)-ethane, or of condensation products of phenols with formaldehyde which are obtained under acid conditions, such as phenol novolacs and cresol novolacs; di- and poly-($\beta$-methylglycidyl) ethers of the abovementioned polyhydric alcohols or polyhydric phenols; polyglycidyl esters of polybasic carboxylic acids, such as phthalic acid, terephthalic acid, $\Delta^4$-tetrahydrophthalic acid and hexahydrophthalic acid; N-glycidyl derivatives of amines, amides and heterocyclic nitrogen bases, such as N,N-diglycidylaniline, N,N-diglycidyltoluidine or N,N,N',N'-tetraglycidyl-bis-(p-aminophenyl)-methane; triglycidyl isocyanurate; N,N'-diglycidylethyleneurea; N,N'-diglycidyl-5,5-dimethylhydantoin and N,N'-diglycidyl-5-isopropylhydantoin; and N,N'-diglycidyl-5,5-dimethyl-6-isopropyl-5,6-dihydro-uracil.

Further suitable epoxide compounds are alicyclic diepoxides, such as vinylcyclohexene dioxide, limonene dioxide, dicyclopentadiene dioxide and ethylene glycol bis-(3,4-epoxytetrahydrocyclopentadien-8-yl)-glycidyl ether, and also compounds containing two epoxycyclohexyl radicals, such as diethylene glycol bis-(3,4-epoxycyclohexanecarboxylate), bis-(3,4-epoxycyclohexylmethyl) succinate, 3',4'-epoxy-6'-methylcyclohexylmethyl 3,4-epoxy-6-methyl-cyclohexane-carboxylate and 3',4'-epoxyhexahydrobenzal-3,4-epoxycyclohexane-1,1-dimethanol.

In the following examples parts are by weight: percentages are by weight unless stated otherwise.

A. Preparation of the metal/amine complexes

EXAMPLE 1

Complex compound A 17.88 g (0.05 mol) of the Zn salt of pyrrolidone-5-carboxylic acid (contains 10.06% by weight of water of crystallisation) and 101 g (0.05 mol) of polyoxypropylenediamine, which has an amine content of 0.99 equivalent of amino group/kg and is obtainable under the tradename "Jeffamine D-2000" from the Jefferson Chemical Co., in 80 ml of methanol are reacted for 1 hour at 67° C. in a glass apparatus which is fitted with a stirrer, a thermometer and a reflux condenser. The clear yellowish solution is then concentrated in a rotary evaporator at 94° C. in vacuo and the resulting residue is dried to constant weight at 100° C./0.1 mm Hg. This yields 116.6 g (99.6% of theory) of a yellow, viscous, clear amine complex with an amine content of 0.825 equivalent of amino group/kg.

| Elementary analysis: | calculated | found |
|---|---|---|
| | 2.40% N | 2.66% N |
| | 2.79% Zn | 2.72% Zn |

$C^{13}$-NMR data

The differences in the $\delta_c$ values of the metal salt/amine complex and the polyoxypropylenediamine in the region of the amino group (NCH, NCH$_2$, N.CH.=CH$_3$) are significant and indicate complex formation between the diamine and the Zn salt.

| $\delta_c$ | Assigned to |
|---|---|
| 18.6 | N . CH . $\underline{C}$H$_3$ |
| 47.9 | NCH, NCH$_2$ |
| 47.6 | |

The $C^{13}$-NMR spectrum is in accord with the following complex structure:

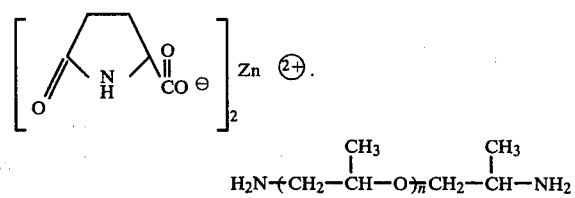

$n$ = approximately 33.1

EXAMPLE 2

Complex compound B 230 g (0.70 mol) of the Zn salt of pyrrolidone-5-carboxylic acid (contains 2.13% by weight of water of crystallisation) and 278.6 g (0.70 mol) of polyoxypropylenediamine (amine content: 5.02 equivalents of amino groups/kg), which is obtainable under the tradename "Jeffamine D-400" from the Jefferson Chemical Co., are reacted in 840 ml of methanol for 1 hour and 55 minutes at 66° C. The reaction mixture is worked up analogously to Example 1 and this yields 491.5 g (97.6% of theory) of a clear, yellow, very highly viscous amine complex, the amine content of which is 2.84 equivalents of amino group/kg.

| Elementary analysis: | calculated | found |
|---|---|---|
| | 7.79% N | 7.65% N |
| | 9.08% Zn | 8.33% Zn |

The metal salt/amine complex has the following structure:

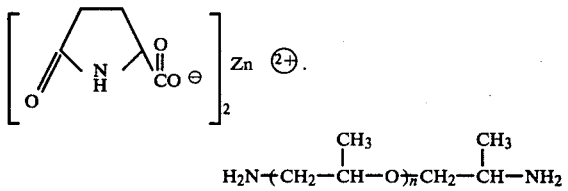

n = approximately 5.6

EXAMPLE 3

Complex compound C

Analogously to Example 1, 17.88 g (0.05 mol) of the Zn salt of pyrrolidone-5-carboxylic acid (contains 10.06% by weight of water of crystallisation) and 11.68 g (0.05 mol) of polyoxypropylenediamine (amine content: 8.56 equivalents of amino groups/kg), which is obtainable under the tradename "Jeffamine D-230" from the Jefferson Chemical Co., in 50 ml of methanol are reacted for 1 hour and 39 minutes at 67° C. The reaction mixture is worked up as described in Example 1 and this yields 27.8 g (100% of theory) of a solid, glassy amine complex with an amine content of 3.58 equivalents of amino groups/kg (99.4% of theory).

| Elementary analysis: | calculated | found |
|---|---|---|
| | 10.09% N | 10.01% N |
| | 11.77% Zn | 11.15% Zn |

The amine complex has the following structure:

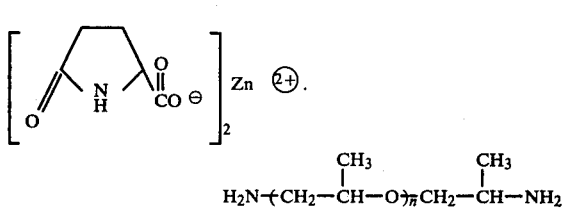

n = approximately 2.6

EXAMPLE 4

Complex compound D 18.99 g (0.05 mol) of the Zn salt of benzenesulphonic acid and 95.33 g (0.05 mol) of polyoxypropylenediamine (amine content: 1.049 equivalents of amino groups/kg), which is obtainable under the tradename "Jeffamine D-2000" from the Jefferson Chemical Co., in 100 ml of dimethylformamide are allowed to react for 1 hour and 35 minutes at 131°–133° C. The reaction mixture is worked up analogously to Example 1 and this yields 111.2 g (97.28% of theory) of a brownish, viscous amine complex with an amine content of 0.885 equivalent of amino groups/kg.

| Elementary analysis: | calculated | found |
|---|---|---|
| | 1.23% N | 1.15% N |
| | 2.80% S | 2.80% S |
| | 2.86% Zn | 2.76% Zn |

The analytical data and the $C^{13}$-NMR spectrum are in accord with the following structure:

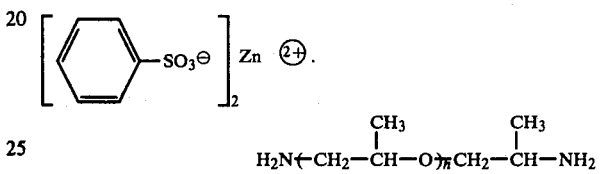

n = approximately 33.1

EXAMPLE 5

Complex compound E 141.7 g (0.50 mol) of the Zn salt of monomethyl methanephosphonate and 209.6 g (0.50 mol) of polyoxypropylenediamine (amine content: 4.77 equivalents of amino groups/kg), which is obtainable commercially under the name "Jeffamine D-400", in 1,000 ml of methanol are allowed to react for 2 hours and 5 minutes at 65° C. After working up according to Example 1, 343.7 g (97.8% of theory) of a slightly yellowish, viscous amine complex are obtained, the amine content of which is 2.99 amino group equivalents/kg.

| Elementary analysis: | calculated | found |
|---|---|---|
| | 3.99% N | 4.05% N |
| | 8.82 P | 8.85% P |
| | 9.30% Zn | 9.10% Zn |

The compound has the following structure:

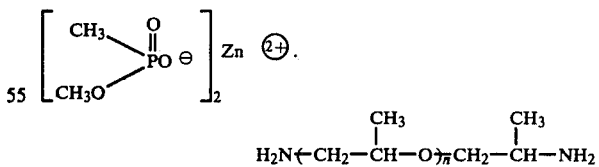

n = 5.6

EXAMPLE 6

Complex compound F 8.1 g (0.025 mol) of the Zn salt of pyrrolidone-5-carboxylic acid (contains 0.6% by weight of water of crystallisation) and 18.8 g (0.025 mol) of polyethylene glycol bis-(γ-aminopropyl) ether (amine content: 2.66 equivalents of amino groups/kg) in 30 ml of methanol are allowed to react as in Example 2 and, after analogous working up, 26.2 g (97.6% of theory) of a clear, yellowish, highly viscous amine complex are obtained, the amine content of which is 1.96 equivalents of amino groups/kg.

| Elementary analysis: | calculated | found |
|---|---|---|
| | 5.22% N | 5.38% N |
| | 6.09% Zn | 5.94% Zn |

Analytical data and the $C^{13}$-NMR spectrum are in accord with the following structure:

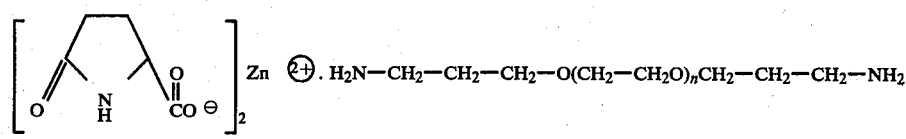

n=approximately 13.2

EXAMPLE 7

Complex compound G 72.5 g (0.22 mol) of the Ni salt of pyrrolidone-5-carboxylic acid (contains 4.64% by weight of water of crystallisation) and 440 g of polyoxypropylenediamine (amine content: 1.00 equivalent of amino groups/kg), which is obtainable commercially as "Jeffamine D-2000", in 1,000 ml of methanol are stirred for 1 hour and 40 minutes at 65° C. The reaction mixture is then worked up analogously to Example 1 and this yields 501.4 g (98.45% of theory) of a clear, green, viscous amine complex with an amine content of 0.90 equivalent of amino groups/kg.

| Elementary analysis: | calculated | found |
|---|---|---|
| | 2.42% N | 2.49% N |
| | 2.54% Ni | 2.31% Ni |

The amine complex has the following structure:

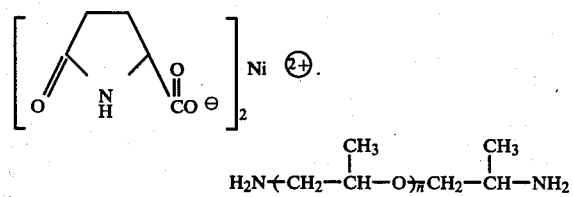

n=approximately 33.1

EXAMPLE 8

Complex compound H

Analogously to Example 1, 19.0 g (0.05 mol) of the Zn salt of succinimidylacetic acid (contains 0.98% of water of crystallisation), 105.3 g (0.05 mol) of polyoxypropylenediamine (amine content: 0.949 equivalent of amino groups/kg) and 200 ml of methanol are reacted for 4 hours and 25 minutes at 65° C. The solution is then filtered and the filtrate is worked up as in Example 1. This yields 116.4 g (93.6% of theory) of a clear, yellowish, viscous amine complex, the amine content of which is 0.81 equivalent of amino groups/kg.

| Elementary analysis: | calculated | found |
|---|---|---|
| | 2.26% N | 2.27% N |
| | 2.63% Zn | 2.51% Zn |

The amine complex has the following structure:

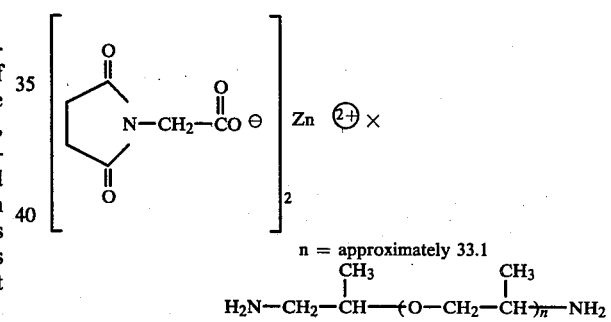

n=approximately 33.1

EXAMPLE 9

Complex compound I

In the manner described in Example 1, 32.4 g (0.1 mol) of the Zn salt of pyrrolidone-5-carboxylic acid (contains 0.6% by weight of water of crystallisation), 97.3 g (0.1 mol) of polyoxyethylenediamine, which has an amine content of 2.056 equivalents of amino groups/kg and is obtainable under the tradename "Jeffamine ED-900" from the Jefferson Chemical Co., and 100 ml of methanol are reacted for 1 hour and 30 minutes at 67°–68° C. The reaction mixture is worked up as in Example 1 and this yields 127.3 g (97.9% of theory) of a yellow, viscous, clear amine complex, which has an amine content of 1.55 equivalents of amino groups/kg.

| Elementary analysis: | calculated: | found: |
|---|---|---|
| | 4.35% N | 4.29% N |
| | 5.07% Zn | 4.48% Zn |

The amine complex has the following structure:

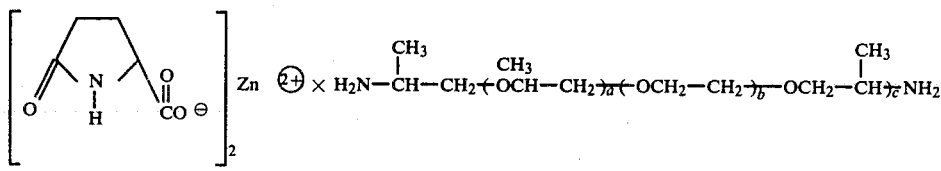

b=20.5   a+c=3.5

EXAMPLE 10

Complex compound J 10.8 g (0.02 mol) of the Zn salt of 6-(3',4'-dimethyl-maleimido)-hexanecarboxylic acid, 42.1 g (0.02 mol) of polyoxypropylenediamine ("Jeffamine D-2000", amine content: 0.95 equivalent of amino groups/kg) and 100 ml of 2-ethoxyethanol are reacted for 30 minutes at 104°–111° C. The reaction mixture is filtered and the filtrate is worked up analogously to Example 1. This yields 49.8 g (98.22% of theory) of a clear reddish, viscous amine complex, the amine content of which is 0.715 equivalent of amino groups/kg.

| Elementary analysis: | calculated: | found: |
|---|---|---|
| | 2.21% N | 2.03% N |
| | 2.58% Zn | 2.48% Zn |

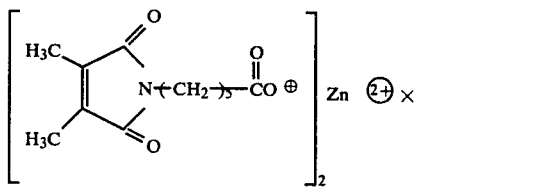

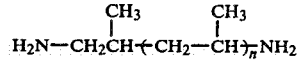

n=approximately 33.1

EXAMPLE 11

Complex compound K 4.7 g (0.02 mol) of the Zn salt of cyanoacetic acid, 42.1 g (0.02 mol) of polyoxypropylenediamine ("Jeffamine D-2000", amine content: 0.95 equivalent of amino groups/kg) and 70 ml of methanol are reacted for 10 minutes at 64° C. and the reaction mixture is worked up as in Example 1. This yields 46.4 g (99.2% of theory) of a yellow, clear, highly viscous amine complex, the amine content of which is 0.86 equivalent of amino groups/kg.

| Elementary analysis: | calculated: | found: |
|---|---|---|
| | 2.40% N | 2.18% N |
| | 2.80% Zn | 2.68% Zn |

The amine complex has the following structure:

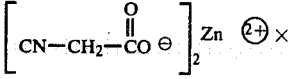

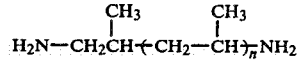

n=approximately 33.1

EXAMPLE 12

Complex compound L 8.0 g (0.02 mol) of the Co salt of p-toluenesulphonic acid (contains 0.97 percent by weight of water of crystallisation), 42.1 g (0.02 mol) of polyoxypropylenediamine ("Jeffamine D-2000", amine content: 0.95 equivalent of amino groups/kg) and 100 ml of methanol are reacted for 3 hours and 30 minutes at 64° C. The reaction mixture is filtered and the filtrate is worked up as in Example 1. This yields 46.9 g (98.3% of theory) of a brownish viscous amine complex with an amine content of 0.68 equivalent of amino groups/kg.

| Elementary analysis: | calculated | found: |
|---|---|---|
| | 1.16% N | 1.01% N |
| | 2.65% S | 2.68% S |
| | 2.44% Co | 2.12% Co |

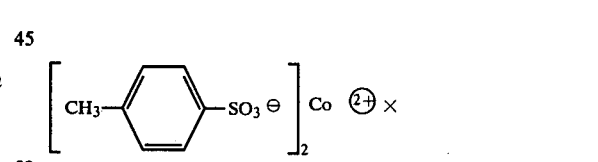

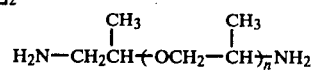

n=approximately 33.1

B. Use of the metal salt/amine complexes

EXAMPLE I

Portions of 100 parts of a liquid bisphenol A diglycidyl ether resin with an epoxide content of 5.2 equivalents/kg are mixed with 10 and with 25 parts of the complex compound A prepared in Example 1. For this purpose, the complex compound A, which is of medium viscosity, is introduced into the epoxide resin, which has been prewarmed to about 40° C., with stirring. A completely homogeneous solution is already obtained after about 5 minutes. The processing properties and end properties of these formulations are listed in Table I below.

Table I

Epoxide resin/complex compound A: processing properties and end properties as a function of the proportion of curing agent

| Formulation | 100 parts of epoxide resin 25 parts of complex A | 100 parts of epoxide resin 10 parts of complex A |
|---|---|---|
| Initial viscosity at 40° C. (cP) | 4240 | 2640 |
| Pot life at 40° C. up to 15,000 cP | 64 hours | 70 days |
| Curing (hours/°C.) | 2/160 + 8/180° | 2/160 + 8/180° |
| Flexural strength according to VSM 77,103 (kg/mm$^2$) | 8.2 | 12.2 |
| Deflection according to VSM 77,103 (mm) | 8.8 | 7.4 |
| Impact strength VSM 77,105 (cmkg/cm$^2$) | 16.3 | 15.5 |
| Tensile strength according to VSM 77,101 (kg/mm$^2$) | 3.8 | 4.1 |
| Elongation at break according to VSM 77,101 (%) | 2.6 | 1.4 |
| Heat distortion point according to Martens, DIN 55,458 (°C.) | 61 | 124 |
| Absorption of water, 4 days/25° C. (%) | 0.3 | 0.19 |
| Tensile shear strength according to VSM 77,101 (kg/mm$^2$) | 2.2 | 2.1 |
| Dielectric loss factor tan δ 1% value (°C.) | 105 | 150 |
| 10% value (°C.) | 183 | 200 |
| Glass transition temperature (%) | | 163* |

*The formulation is completely cured; no exothermic secondary reaction detectable As can be seen from the table, both the pot life of the curable formulations and the properties of the cured formulations can be varied by the amount of the complex compounds employed. The cured formulations in general have advantageous mechanical and dielectric properties and the high Martens value which is obtained for the cured formulations when catalytic amounts of the complex compound are used is to be singled out.

COMPARISON EXAMPLES

Comparison A

Use of different amounts of polyoxypropylenediamine as the curing agent

Portions of 100 parts of the bisphenol A diglycidyl ether used in Example I are mixed with different amounts of the polyoxypropylenediamine contained in complex compound A, specifically (a) with the stoichiometric amount (=265 parts)
(b) with 2/5 of the stoichiometric amount (=106 parts) and
(c) with those amounts which are contained in 10 and in 25 parts of the complex compound A (=8.62 and 21.6 parts respectively).

Processing and curing of these mixtures led to the following results:

(a) 100 parts of epoxide resin per 265 parts of polyoxypropylenediamine

The pot life of this formulation at room temperature is good (>28 days), but the cured products have significantly poorer properties. After extensive curing (2 hours at 120° C. and 6 hours at 100° C.), very soft test pieces are obtained which cannot be subjected to mechanical stress:

| Martens value according to DIN 55,458 | 23° C. |
|---|---|
| Dielectric loss factor | |
| tan δ  1% value | ⎫ cannot be tested |
| 10% value | ⎭ |
| Absorption of water, 4 days/25° C. | 2.1% |

(b) 100 parts of epoxide resin per 106 parts of polyoxypropylenediamine

This formulation also has a good storage stability; however it is not curable but remains liquid even after extensive curing.

(c) 100 parts of epoxide resin per 8.62 and per 21.6 parts of polyoxypropylenediamine The formulations have properties analogous to those of formulation (b). They are stable on storage but not curable.

Comparison B

Use of mixtures of the zinc salt of pyrrolidonecarboxylic acid and polyoxypropylenediamine as the curing agent Portions of 100 parts of the bisphenol A diglycidyl ether used in Example I are mixed with those amounts of the Zn salt of pyrrolidonecarboxylic acid and polyoxypropylenediamine which are contained in 10 parts and in 25 parts of the complex compound A.

| Formulation | (a) | (b) |
|---|---|---|
| Epoxide resin | 100 parts | 100 parts |
| Zn salt of pyrrolidonecarboxylic acid | 1.38 parts | 3.45 parts |
| Polyoxypropylenediamine | 8.62 parts | 21.6 parts |

Since the zinc salt of pyrrolidonecarboxylic acid is not soluble in the epoxide resin at room temperature, the particular amounts of this compound are mixed intensively with the epoxide resin and the amine is then stirred in at room temperature. The resulting final formulations are thus dispersions at room temperature and therefore differ substantially from the two formulations of Example 1. These dispersions have a good stability on storage at room temperature (>28 days). After a curing cycle of 2 hours at 160° C.+8 hours at 180° C., the moulded pieces have the following measured values:

|  | Formulation (a) | Formulation (b) |
|---|---|---|
| Martens value according to DIN 55,458 | 41° C. | 55° C. |
| Dielectric loss factor tan δ |  |  |
| 1% value | 42° C. | 71° C. |
| 10% value | 166° C. | 139° C. |

Comparison C

Use of the complex compound described in U.S. Pat. No. 2,819,233 (complex I) as a curing agent for epoxide resins For comparison, a complex I is prepared in accordance with the instructions given in the U.S. Patent under "Complex A" and is processed as in Example IV of the U.S. Patent.

Complex I

The zinc salt of 2-ethylhexanoic acid is prepared from 1 mol of zinc oxide and 2 mols of 2-ethylhexanoic acid in 475 g of xylene. 1 mol of diethylenetriamine is added to this solution, with stirring, and the whole is reacted for 35 minutes at 120° C. After drying at 50° C., the complex still contains about 5% of xylene and has a diethylenetriamine content of 6.44 equivalents/kg.

100 parts of the bisphenol A diglycidyl ether used in Example I of this specification are mixed with 20 parts of complex I, corresponding to the mixing ratio of 0.25 equivalent of active amino group per 1 epoxide equivalent which is indicated in Example IV of the U.S. Patent, and the mixture is cured for 8 hours at 200° C. in order to achieve complete crosslinking. The pot life of this formulation at 40° C. and up to 15,000 cP is 26 hours. The resulting moulded pieces have a glass transition temperature of 109° C.

When measuring the glass transition temperature, it was found that, in contrast to the formulations in Example I, the above formulation containing the complex I has not yet completely cured under the indicated curing conditions since exothermic secondary reactions are still clearly discernible.

EXAMPLE II

Portions of 100 parts of the bisphenol A diglycidyl ether used in Example I are mixed with 10 and with 25 parts of the complex compound E prepared in Example 5. For this purpose, the complex compound, which is of medium viscosity, is added to the resin and the whole is stirred until everything has completely dissolved. In order to effect rapid dissolving of the complex, the epoxide resin can be pre-warmed to 40° C.—but this is not absolutely necessary. After curing for 24 hours at 80° C. and 4 hours at 180° C., moulded pieces are obtained which have the following characteristic values:

| Formulation | 100 parts of epoxide resin 10 parts of complex E | 100 parts of epoxide resin 25 parts of complex E |
|---|---|---|
| Martens value according to DIN 55,458 | 106° C. | 87° C. |
| Absorption of water, 4 days/25° C. | 0.10% | 0.14% |
| Dielectric loss factor tan δ |  |  |
| 1% value | 132° C. | 106° C. |
| 10% value | 197° C. | 185° C. |

What is claimed is:
1. A metal salt/amine complex of the formula I

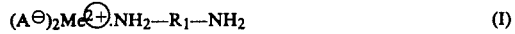

wherein A denotes an anion of the formula selected from the group consisting of

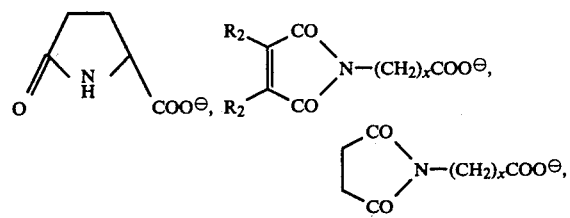

in which x=a number from 1 to 5 in each case and $R_2=$—H or methyl,

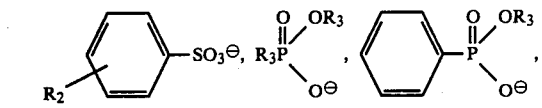

in which $R_2=$—H or methyl and $R_3=$alkyl having 1 to 4 C atoms in each case, and N≡C—CH$_2$—COO$^\ominus$, Me$^{2+}$ denotes a divalent metal cation selected from the group consisting of Zn, Co, Cu, Ni and Cd and R$_1$ is a polyoxyalkylene radical of the formula selected from the group consisting of

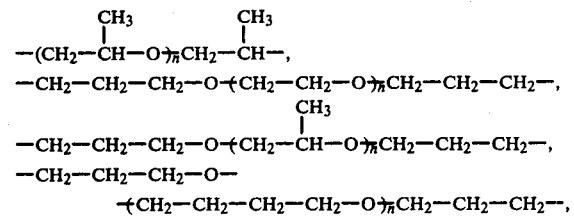

in which n=a number from 2 to 35 in each case, and

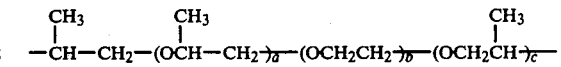

in which b=a number from 10 to 50 and the sum of a and c is a number from 2 to 4.

2. A complex according to claim 1, wherein A in formula I denotes an anion of the formula

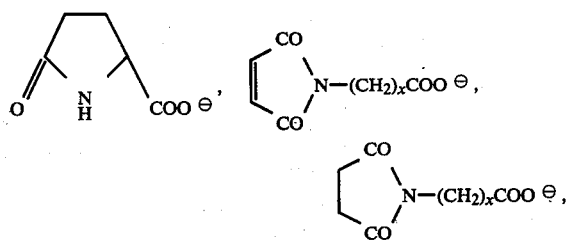

in which x=a number from 1 to 5 in each case,

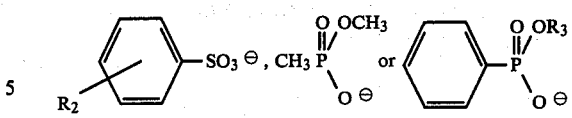

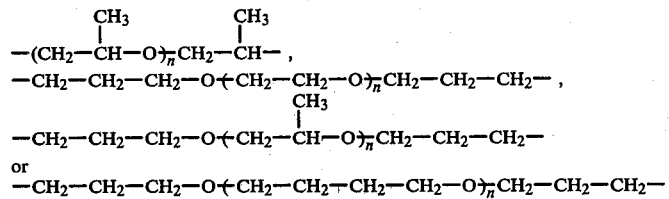

in which $R_2=$—H or methyl and $R_3=$alkyl having 1 to 4 C atoms in each case.

3. A complex according to claim 1, wherein A denotes the anion of pyrrolidonecarboxylic acid, benzenesulphonic acid or toluenesulphonic acid or of a methanephosphonic acid monoester.

4. A complex according to claim 1, wherein $Me^{\oplus}$ denotes a divalent metal cation of Zn.

5. A complex according to claim 1, wherein $R_1$ denotes a polyoxyalkylene radical of the formula $$-(CH_2-\underset{\underset{CH_3}{|}}{CH}-O)_n CH_2-\underset{\underset{CH_3}{|}}{CH}-,$$
$$-CH_2-CH_2-CH_2-O(CH_2-CH_2-O)_n CH_2-CH_2-CH_2-,$$
$$-CH_2-CH_2-CH_2-O(CH_2-\underset{\underset{CH_3}{|}}{CH}-O)_n CH_2-CH_2-CH_2-$$
or
$$-CH_2-CH_2-CH_2-O(CH_2-CH_2-CH_2-CH_2-O)_n CH_2-CH_2-CH_2-$$

in which n=a number from 2 to 35 in each case.

6. A complex according to claim 1, wherein $R_1$ denotes a polyoxyalkylene radical of the formula

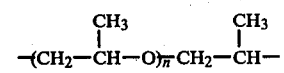

in which n is a number from 2 to 35.

* * * * *